United States Patent [19]
Potter et al.

[11] Patent Number: 4,574,130
[45] Date of Patent: Mar. 4, 1986

[54] POLYMERIZABLE COMPOUNDS

[75] Inventors: William D. Potter, Bishops Stortford; Sinan B. Kiamil, Harlow, both of United Kingdom

[73] Assignee: Smith & Nephew Associated Companies P.L.C., United Kingdom

[21] Appl. No.: 557,142

[22] PCT Filed: Jun. 30, 1983

[86] PCT No.: PCT/GB83/00165
§ 371 Date: Nov. 7, 1983
§ 102(e) Date: Nov. 7, 1983

[87] PCT Pub. No.: WO84/00163
PCT Pub. Date: Jan. 19, 1984

[30] Foreign Application Priority Data
Jul. 3, 1982 [GB] United Kingdom ............... 8219303

[51] Int. Cl.$^4$ ........................... C08F 222/20
[52] U.S. Cl. ............................. 523/111; 524/831; 524/833; 526/240; 526/307.5; 526/318; 526/311
[58] Field of Search ............ 526/318, 240, 307.5, 526/311; 523/111; 524/833, 831

[56] References Cited

U.S. PATENT DOCUMENTS

| | | | |
|---|---|---|---|
| 2,524,921 | 10/1950 | Minter | 526/318 |
| 3,150,118 | 9/1964 | Clemens | 526/318 |
| 3,790,533 | 2/1974 | Samour | 526/318 |
| 4,292,419 | 9/1981 | Kamada | 526/240 |
| 4,384,096 | 5/1983 | Sonnabend | 526/318 |
| 4,463,150 | 7/1984 | Kelly | 526/318 |

FOREIGN PATENT DOCUMENTS

| | | | |
|---|---|---|---|
| 41871 | 12/1981 | European Pat. Off. | |
| 49-121886 | 11/1974 | Japan | 526/318 |
| 991904 | 9/1961 | United Kingdom | 526/318 |

OTHER PUBLICATIONS
Derwent Abstract AN 31388v/17.

Primary Examiner—C. Warren Ivy
Attorney, Agent, or Firm—Jacobs & Jacobs

[57] ABSTRACT

Compounds of the formula:

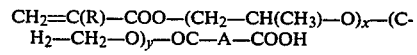

$$CH_2=C(R)-COO-(CH_2-CH(CH_3)-O)_x-(CH_2-CH_2-O)_y-OC-A-COOH$$

or a salt thereof, wherein
R is H or $CH_3$,
x is an integer from 2 to 20.
y is an integer from 0 to 5,
A is an alkylene, alkenylene, or phenylene radical such that $A(COOH)_2$ is a dibasic acid capable of forming an anhydride $(A(CO)_2O$, are described. These are polymerizable compounds which have also surfactant properties. The compounds may be used to replace non-polymerizible surfactants in emulsion polymerization reactions, and preferably in those reactions which result in adhesive polymers which are suitable for surgical and medical use. Methods for preparing the compounds and pressure sensitive adhesives formed by copolymerization of the compounds with other acrylate monomers are also described.

7 Claims, No Drawings

POLYMERIZABLE COMPOUNDS

The present invention relates to polymerisable compounds which are also surfactants, adhesive copolymers thereof for surgical and medical use, and methods of manufacturing the same.

It is well known in the art to form polymers by emulsion polymerisation. Such processes are convenient because they avoid the use of solvents. The emulsion polymerisation process requires the use of a surfactant to form stable emulsion of monomers and other ingredients and to prevent coagulation of the polymer emulsion thus formed; usually a non-polymerisable surfactant is used. However, the residual surfactant in the polymer can be extracted by water and therefore renders the polymer sensitive to water. To minimise this problem the use of polymerisable surfactants has been proposed in the patent literature. For example, British Patent No. 1,430,136 discloses emulsion polymerised polymers as adhesives and lists copolymerisable surfactants suitable for this purpose.

Specific anionic copolymerisable surfactants which can also be used to form stable emulsions in emulsion polymerisation have now been discovered; these are readily copolymerisable, as is desirable in such surfactants.

However, although the art teaches the use of copolymerisable surfactants, the need for external non-copolymerisable surfactants has not hitherto been successfully avoided, although this would clearly be desirable.

All the examples given in the aforementioned patent show the use of copolymerisable surfactants in combination with an external non-copolymerisable surfactant.

The present surfactants can be used to form stable emulsions in emulsion polymerisation without the need for external non-copolymerisable surfactants additional thereto.

The present invention thus provides a compound having the formula (I):

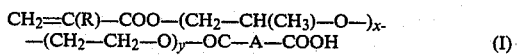

or a salt thereof, wherein R is H or $CH_3$, x is an integer from 2 to 20, y is an integer from 0 to 5, A is an alkylene, alkenylene, or phenylene radical such that A $(COOH)_2$ is a dibasic acid capable of forming an anhydride A $(CO)_2$ O.

Apt salts of compounds of formula (I) are water soluble and include the ammonium, water soluble alkyl substituted ammonium and akali metal salts thereof. Favoured salts of the compound of the formula (I) are the ammonium, trimethyl-ammonium, triethyl-ammonium, sodium and potassium salts. A preferred salt of the compounds of the formula (I) is the ammonium salt. Another preferred salt is the sodium salt.

The water insoluble compounds of the invention can be used as intermediates to form the water soluble compounds of the invention by ion exchange. Tne compound of formula (I) itself is water insoluble.

Preferably R is $CH_3$.

Favoured residues A are alkylene or akenylene groups of 2 to 6 carbon atoms or pheneylene. Preferred residues A are $CH_2CH_2$, $CH=CH$ or ortho-$C_6H_4$. The most preferred residue A is $CH_2CH_2$.

A favoured value for y is 0.

Favoured values for x are 3 to 10 and more favourably 5 to 9. A preferred value for x is 7.

All values such as x and y in oligomers and polymers herein are number average values.

A highly favoured compound of this invention is the ammonium or sodium salt of compounds of formula (I) in which x is an integer from 3 to 10, y is 0, A is $-CH_2-CH_2-$, $-CH=CH-$ or $-C_6H_4-$. Preferred compounds of the invention are the ammonium salts of methacryloyl poly (oxypropylene) hemi succinate esters. Such compounds are favourably provided as a mixture of esters of different chain lengths containing a number average of 3 to 10 oxypropylene units per molecule. A preferred compound of this type contains a number average of 7 oxypropylene units per molecule.

Water soluble compounds of the invention are surfactants. The ammonium and alkali metal, especially the sodium salt compounds in particular have good surfactant properties. Tne ammonium salt and tne sodium salt are especially favoured for this purpose.

The surfactant compounds of the present invention can be used in emulsion polymerisation, when they will become part of the resulting polymer molecule.

Therefore in one aspect, the invention provides a polymer which comprises residues of a compound of formula (I) or a salt thereof.

The surfactant compounds of the present invention can be used advantageously in the emulsion polymerisation of acrylic monomers. It has been found that these compounds will form stable emulsions with acrylic monomers and will prevent coagulation of any such emulsions during an emulsion polymerisation process.

Apt acrylic monomers include optionally hydroxylated alkyl esters, or amides, or acrylic and methacrylic acids.

A polymer produced by emulsion polymerisation using a surfactant of the present invention may be an adhesive polymer, advantageously an acrylic adhesive polymer.

Apt acrylic monomers for such adhesive polymers include those listed above.

The surfactant compounds of the invention employed during the emulsion polymerisation process will become part of the resulting adhesive polymer molecule.

Therefore in another aspect the invention provides an adhesive polymer which comprises residues of one or more acrylic monomers and residues of one or more compounds of formula (I) or a salt thereof.

Adhesive polymers of this type may be pressure sensitive adhesive polymers.

Aforementioned British Pat. No. 1,430,136 discloses the use of copolymerisable surfactants together with non-copolymerisable surfactants in forming pressure sensitive adhesives for masking tapes.

Some pressure sensitive adhesives may be used on skin, for example in surgical or medical dressings. However, in order to maintain good adhesion to skin it is especially desirable that such adhesives are not water-sensitive, and that the use of external non-copolymerisable surfactants for emulsion-polymerised pressure sensitive adhesives is therefore avoided.

The aforementioned patent does not therefore disclose pressure-sensitive adhesives for use on skin, for example in surgical or medical dressings.

The water soluble compounds of the invention can be readily copolymerised with one or more acrylic monomers by emulsion polymerisation to form adhesive materials suitable for use on skin.

The use of an ammonium salt of the invention to form an adhesive polymer of the invention is specially advantageous in that on heating the polymer in a dry form, ammonia is liberated and the adhesive polymer is converted to the acid form. The acid form of tne adhesive polymer of the invention is generally less sensitive to water than analogous polymers containing salts of the acid.

The adhesive polymer of the invention may suitably contain 0.5 to 10% by weight, preferably 0.6 to 6% by weight of residues of a compound of formula (I) or a salt thereof, for example 0.7 to 5%. For a compound of formula (I) itself or a salt readily converted thereto, for example the ammonium salt, the polymer may preferably contain 2 to 6% by weight, in particular 2 to 4%, for example 3 to 4%. For other salts of the compound of formula (I) suitable examples include 0.8 to 3% by weight, in particular 0.8 to 1.5%.

In apt polymers of the invention the acrylic polymer component consists mainly of acrylic residues for which the monomer is a alkyl ester of acrylic or methacrylic acid in which the alkyl residue contains 2 to 10 carbon atoms. Favoured pressure sensitive adhesive forming alkyl acrylate monomers are alkyl esters of acrylic acid in which tne alkyl group contains 3 to 12 carbons atoms and preferably 4 to 9 carbon aroms. Alkyl acrylate monomers of this type include n-butyl acrylate, 2-ethylhexyl acrylate and other octyl acrylates, favourably n-butyl acrylate and 2-ethylhexyl acrylate.

A suitable pressure sensitive adhesive polymer may comprise 90 to 99.5% by weight of such acrylic residues, favourably 94 to 99.5% and preferably 96 to 99.5%.

Often these acrylic residues will consist of a mixture of two monomer species, often in equal proportions.

Pressure sensitive adhesives of the invention advantageously contain residues of other acrylic monomers. Suitable monomers include acrylic esters, comprising monoesters such as optionally hydroxylated or alkoxylated alkyl esters, for example methylmethacrylate, ethylmethacrylate, hydroxyethyl methacrylate and methoxyethyl methacrylate; and polyesters such as alkanediyl or poly PEG diesters, for example butane-1,4-diyl diacrylate, hexane-1,6-diyl diacrylate, polyethylene glycol diacrylates, and glycidyl methacrylate. Suitable monomer residues also include acrylic amides, comprising monoamides such as optionally N-alkylated amides, for example acrylamide, methacrylamide, N-tert. butylacrylamide and N-laurylacrylamide. Preferred monomers include acrylamide and hydroxyethyl methacrylate.

Such residues may form up to 10% by weight of the polymer, for example up to 5%, aptly 0.2 to 4%. The most apt proportion of such residues will depend to some extent on the particular monomer species, the monomer species of the main components, the emulsion polymerisation conditions and the desired physical properties of the pressure sensitive adhesives. The apt range 0.2 to 4% therefore includes tne ranges 0.2 to 1% by weight and 1 to 4%, the latter including tne ranges 1 to 1.5% and 1.5 to 3%, which are more or less apt, depending on the foregoing factors. For acrylic amide residues values more aptly span the ranges 0.2 to 1% and 1 to 1.5% by weight, preferably 0.3 to 0.8%. For acrylic ester residues values more aptly span the ranges 0.8 to 1%, 1 to 1.5% and 1.5 to 3% by weight, preferably 0.8 to 1.5%.

A suitable pressure sensitive adhesive polymer comprises 39 to 59% by weight of n-butyl acrylate residues, 39 to 59% by weight of 2-ethylhexyl acrylate residues, 0.3 to 10%, aptly 0.3 to 5% by weight of acrylamide or hydroxyethylmethacrylate residues and 1 to 5% by weight of residues of a methacrylylpoly(oxypropylene) succinate mono-ester containing an average of 7 oxypropylene units per molecule (A) or the ammonium salt thereof, or 0.8 to 3% by weight of the corresponding sodium salt.

A favoured pressure sensitive adhesive polymer comprises 47 to 49.75% by weight of n-butyl acrylate residues, 47 to 49.75% by weight of 2-ethylhexyl acrylate residues, 0.3 to 1.5% by weight of acrylamide residues or 0.8 to 3% by weight of hydroxyethyl methacrylate residues, and 2 to 4% by weight of (A) or the ammonium salt thereof, or 0.8 to 1.5% by weight of the corresponding sodium salt.

Preferred pressure sensitive adhesive polymers of the invention contain: 49, 49, 1 and 1% by weight respectively of the above residues, the last two being respectively hydroxyethyl methacrylate and the sodium salt of (A); and 48.25, 48.25, 0.5 and 3% by weight respectively, the last two being respectively acrylamide and (A) or its ammonium salt.

The pressure sensitive adhesives of the invention can be used for adhesive surgical and medical dressings and therefore adhesive surgical and medical dressings employing an adhesive of this invention are an important aspect of this invention.

Tne adhesive of the invention may be used to coat fabrics, porous polyvinylchloride film, polyurethane film, integral nets and the like to form surgical and medical adhesive dressings. Suitable backing materials for moisture vapour transmitting adhesive dressings are disclosed in British Pat. No. 1,280,631.

The compounds of the formula (I) can be prepared by a process which comprises reacting a dibasic acid anhydride of the formula $A(CO)_2O$ wherein A is as defined in relation to the compound of formula (I) with a compound of the formula (II):

$$CH=C(R)-COO-(CH_2-CH(CH_3)-O-)_x-(CH_2-CH_2-O)_yH \qquad (II)$$

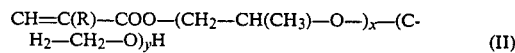

wherein R, x and y are as defined in relation to formula (I).

A favoured polyoxyproplene glycol mono-methacrylate ester having an average of 7 oxypropylene groups per molecule is known compound, reference Bisomer PPM7 available from Stein and Honeywell (of BP Chemicals Limited).

Suitable dibasic acid anhydrides include succinic anhydrde, maleic anlydride and phthalic anhydride. A favoured anhydride is succinic anhydride.

In forming the compounds of the invention the reactants are firstly optionally dissolved in a suitable organic solvent, such as toluene, 1,1,1-trichloroethane, methyl ethyl ketone, or ethyl acetate, favourably toluene or trichloroethane, and preferably toluene. They are then heated under reflux, or preferably at °C. in the presence of a conventional acidic or basic esterification catalyst in a reaction vessel to form the compound of the formula (I). Suitable catalysts include organic bases such as triethylamine or inorganic bases such as sodium carbonate.

In a typical favoured process of forming favoured acid compounds of the invention the reactants are dissolved in toluene and heated under reflux for a period of 6 hours at a temperature of approximately 120° C.

In an alternative typical favoured process the undiluted reactants are heated for approximately 6 hours at approximately 60° C. in the presence of 30% by weight of the total reactants of triethylamine.

The reaction mixture should contain a polymerisation inhibitor for example phenothiazine or, preferably, 4-methoxyphenol to prevent premature polymerisation of the polyoxyproplene glycol mono-acrylate or mono-methacrylate.

The compound of the formula (I) can be obtained from the solution by stripping off the organic solvent by a conventional method for example by means of a rotary evaporator under vacuum. It is desirable to purify the thus produced compound or to remove unreacted starting materials and if necessary the polymerisation inhibitor, if it is not desired to store the product.

The salts of compounds of the formula (I) can be made by reacting the acid compound with the appropriate base. Apt water soluble salt compounds of the invention can be formed by reacting the acid compound in aqueous suspension with an alkali metal hydroxide or optionally alkyl substituted ammonium hydroxide. These are prefereably generated in situ when needed for the relevant emulsion polymerisation process, from the acid which can be stored as a liquid.

Less favourably, the water soluble salts can be stored as aqueous solutions. The aqueous solution can contain an inhibitor such as 4-methoxyphenol to prevent premature polymerisation during storage.

The compounds of the formula (II) may be prepared by any conventional method of the art.

Adhesive polymers of the invention can be prepared by a process which comprises polymerising as an emulsion one or more acrylic monomers and a water soluble salt of a compound of the formula (I) in the presence of a free radical catalyst.

The free radical catalyst is generally a conventional aqueous free radical catalyst such as ammonium persulpate, or may be a redox catalyst.

The emulsion may conveniently be made by initially forming an aqueous solution of a water-soluble salt of the compound of formula (I) in situ from the acid of formula (I) and a suitable basic salifying agent, for example an alkali metal or optionally trialkyl substituted ammonium hydroxide. The optional termonomer in the polymers of tne present invention may then be added to the solution, in particular if it is an acrylic amide, and the remaining monomers to be polymerised then added to the salt solution. Alternatively, all the monomers may be premixed, in particular if the termonomer is an acrylic ester, and the premix then added to the salt solution. In either case the pH of the salt solution is adjusted to approximately pH10 before the addition of remaining or premixed monomers, which are then added under high-shear stirring.

The resulting monomer emulsion typically has a solids content in the range of 20 to 50% by weight.

The resulting monomer emulsion may then be added to an aqueous solution of free-radical catalyst, for example ammonium persulphate, and polymerisation effected by heating, typically to 80° to 95° C., under an inert atmosphere, such as nitrogen or carbon dioxide. Advantageously, the monomer emulsion may be added to the catalyst solution over a period of time during the polymerisation reaction.

The polyacrylate adhesive emulsions of the invention may contain a thickener such as polyacrylate thickener. The adhesive can be coated onto a suitable substrate by a direct or transfer coating process using conventional coating techniques.

The polyacrylate adhesives of the invention containing residues of an ammonium salt of the compound of the invention when heated lose ammonia and the salt is converted to the acid form. Surgical or medical dressings coated with such polyacrylate adhesives have been found to have good adhesion to skin and are not sensitive to water.

EXAMPLE 1

Preparation of polymerisable surfactant

Method A

Polypropylene glycol mono methacrylate containing an average of 7 oxyproplene units per molecule (165 g) succinic anhydride (30 g), phenothiazine (1 g) and toluene were added to a liter reaction flask and heated under reflux for 6 hours at a temperature of approximately 120° C.

The reaction mixture was allowed to cool to room temperature. The toluene was then removed from the mixture using a rotary evaporator under vacuum at a maximum bath temperature of 70° C. to obtain the crude product as the acid.

Concentrated aqueous ammonia solution (35 ml) and distilled water (165 ml) were added to the crude acid to give an aqueous solution. The aqueous solution was extracted with diethyl ether (900 ml) in a separating funnel to remove unreacted starting materials and the phenothiazine inhibitor. The extraction process was repeated twice with further volumes of diethyl ether (150 ml). 4-Methoxyphenol (0.01 g) was added to the aqueous product and residual diethyl ether stripped off using a rotary evaporator under vacuum at a maximum bath temperature of 40° C. The resultant aqueous solution contained approximately 50% by weight of the ammonium salt of methacryloyl poly(oxypropylene) hemisuccinate containing an average of 7 oxypropylene units per molecule. The aqueous solution of ammonium salt was stored in an amber coloured bottle in a cool place away from direct sunlight.

Method B

The reaction procedure of Method A was carried out using 4-methoxyphenol (1%; 2 g) in place of phenothiazine. 1,1,1-Trichloroethane, methyl ethyl ketone and ethyl acetate were also used as alternative solvents to toluene, reaction being carried out at the boiling point of the reaction mixture under solvent reflux.

The crude product obtained after stripping off the solvent was shaken with hexane, the product layer was filtered and the filtered product was washed with hexane. Hexane was removed from the product on a rotary evaporator and the final product was stored as in Method A.

Method C

The procedure of Method B was carried out additionally including triethylamine (1% by weight of total reagents) as catalyst. Yields are in general greater for an equivalent reaction time than in Methods A and B.

Method D

The reaction procedure of Method C was carried out without solvent.

The crude product was used in the emulsion polymerisation of Example 2 without further purification.

EXAMPLE 2

Preparation of emulsion polyacrylate adhesive

Method A

Acrylamide (2 g) and a polymer of Example 1 (3 g) were dissolved in distilled water (100 ml) using sufficient concentrated aqueous ammonia solution to effect solution where the polymer was essentially the free acid. The pH of the solution was adjusted to 10 by the additon of concentrated aqueous ammonia solution 2-Ethylhexyl acrylate (49 g) and n-butyl acrylate (49 g) were added to the solution and the solution stirred with a high shear mixer to form a monomer emulsion. The monomer emulsion was added dropwise from a dropping funnel over a period of 1 hour to an ammonium persulphate solution (0.26 g in 50 ml of distilled water) in a reaction flask fitted with a stirrer and a nitrogen inlet and maintained at a constant temperature in the range of 80° to 90° C. by a constant temperature water bath. The polymerisation reaction was allowed to continue for a further 1½ hours to give a total reaction time of 2½ hours.

After 1½ hours reaction time further concentrated aqueous ammonia solution (2.5 ml) was added.

The resultant polymer emulsion was cooled to 40° C. before being transferred to a storage jar.

Method B

An essentially free acid polymer of Example 1 (1 g) was dissolved in distilled water (100 ml) using sufficient concentrated aqueous sodium hydroxide solution (46–48% w/w) to effect solution. The pH of the solution was adjusted to 10 with the sodium hydroxide solution. 2-Ethylhexyl acrylate (49.5 g), n-butyl acrylate (49.5 g) and hydroxymethyl methacrylate (1 g) were mixed, and the mixture was added to the surfactant solution with high shear mixing.

The remainder of the procedure was as in Method A, with the exception of the addition of further concentrated ammonia solution Polymers having the parts by weight composition shown in Table 1 below were prepared analogously to Method A where the termonomer was an amide and to Method B when it was an ester.

In the table the following abbreviations are used:
2-EHA: 2-ethylhexyl acrylate
n-BA: n-butyl acrylate
HEMA: hydroxyethyl methacrylate
n-LA: n-lauryl acrylamide
AA: acrylamide
NHOX: methacrylylhepta (oxypropylene) succinate mono-ester

TABLE 1

| No | 2-EHA | n-BA | HEMA | n-LA | AA | MHOS | Base |
|---|---|---|---|---|---|---|---|
| 3 | 49.25 | 49.25 | 1.5 | | | 1.0 | NaOH |
| 4 | 47.0 | 47.0 | 6.0 | | | 1.0 | NaOH |
| 5 | 50.0 | 50.0 | | | | 1.0 | NaOH |
| 6 | 48.75 | 48.75 | | | 2.5 | 3.0 | NH₄OH |
| 7 | 48.5 | 48.5 | | | 3.0 | 3.0 | NH₄OH |
| 8 | 48.0 | 48.0 | | | 4.0 | 3.0 | NH₄OH |
| 9 | 49.0 | 49.0 | | | 2.0 | 3.0 | NH₄OH |
| 10 | 49.0 | 49.0 | | | 2.0 | 2.0 | NH₄OH |
| 11 | 49.875 | 49.875 | | | 0.25 | 3.0 | NH₄OH |
| 12 | 49.75 | 49.75 | | | 0.5 | 3.0 | NH₄OH |
| 13 | 49.625 | 49.625 | | | 0.75 | 3.0 | NH₄OH |
| 14 | 49.5 | 49.5 | | | 1.0 | 3.0 | NH₄OH |
| 15 | 49.25 | 49.25 | | | 1.5 | 3.0 | NH₄OH |
| 16 | 49.5 | 49.5 | | 1.0 | | 4.0 | NH₄OH |
| 17 | 49.0 | 49.0 | | 2.0 | | 4.0 | NH₄OH |

EXAMPLE 3

The polyacrylate adhesive emulsion thickened by the addition of an acrylic thickened solution (Primal A S E 60, 10%, available from Rohm and Haas) was coated onto a silicone coated release paper (Stearlese available from Sterling Coated Papers Limited) by means of a blade over flat bed coater and dried in an air circulating oven at a temperature of 110°–5° C. to give a dried pressure sensitive adhesive coating with a weight per unit area of 40 g/m². The adhesive coating was transferred to an integral net backing (Example 2 of British Pat. No. 1,531,715) and cut into 2.5 cm wide surgical tapes.

We claim:

1. An adhesive emulsion polymer of monomers consisting essentially of one or more acrylic monomers selected from the group consisting of acrylic and methacrylic acids or alkyl esters or hydroxyalkyl esters or amides thereof and one or more monomers of the formula (I):

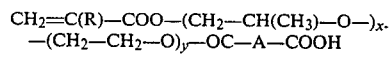

$$CH_2=C(R)-COO-(CH_2-CH(CH_3)-O-)_x-$$
$$-(CH_2-CH_2-O)_y-OC-A-COOH$$

or a salt thereof, wherein
R is H or CH₃,
x is an integer from 2 to 20,
y is an integer from 0 to 5, and A is an alkylene, alkenyl or phenylene radical such that A(COOH)₂ is a dibasic acid capable of forming an anhydride A(CO₂)O.

2. A polymer according to claim 1 which is a pressure-sensitive adhesive polymer of monomers which comprise 39 to 59% by weight of n-butyl acrylate, 39 to 59% by weight of 2-ethylhexyl acrylate, 0.3 to 5% by weight of acrylamide or hydroxyethyl methacrylate and 1 to 5% by weight of a methacrylyl poly(oxypropylene) succinate mono ester containing an average of 7 oxypropylene units per molecule or the ammonium salt thereof.

3. A polymer according to claim 2 wherein said monomers comprise 47 to 49.75% by weight of n-butyl acrylate, 47 to 49.75% by weight of 2-ethylhexyl acrylate, 0.3 to 1.5% by weight of acrylamide or 0.8 to 3% by weight of hydroxyethyl methacrylate, and 2 to 4% by weight of methacrylyl-poly(oxy propylene) succinate mono-ester containing an average of 7 oxypropylene units per molecule or the ammonium salt thereof.

4. An adhesive surgical or medical dressing comprising a pressure-sensitive adhesive polymer according to claim 2.

5. A polymer according to claim 1, which is a pressure-sensitive adhesive polymer of monomers comprising 39 to 59% by weight of n-butyl acrylate, 39 to 59% by weight of 2-ethyl-hexyl-acrylate, 0.3 to 5% by weight of acrylamide or hydroxyethyl methacrylate, and 0.8 to 3% by weight of a methacrylyl poly (oxypropylene) succinate mono ester sodium salt containing an average of 7 oxypropylene units per molecule.

6. A polymer according to claim 5, wherein said monomers comprise 47 to 49.75% by weight of n-butyl acrylate, 47 to 49.75% by weight of 2-ethyl hexyl acrylate, 0.3 to 1.5% by weight of acrylamide or 0.8 to 3% by weight of hydroxyethyl methacrylate, and 0.8 to 1.5% by weight of a methacrylyl-poly(oxypropylene) succinate mono-ester sodium salt containing an average of 7 oxypropylene units per molecule.

7. An adhesive surgical or medical dressing, comprising a pressure-sensitive adhesive polymer according to claim 5.

* * * * *